United States Patent [19]

Bongaarts et al.

[11] Patent Number: 4,786,743

[45] Date of Patent: Nov. 22, 1988

[54] SILVER CATALYST AND A PROCESS FOR PREPARING SAME

[75] Inventors: Jacobus E. Bongaarts, Destelbergen, Belgium; Garmt R. Meima, Amersfoort; John W. Geus, Bilthoven, both of Netherlands

[73] Assignee: The Dow Chemical Company, Midland, Mich.

[21] Appl. No.: 925,194

[22] Filed: Oct. 31, 1986

[51] Int. Cl.⁴ .......................................... C07D 301/10
[52] U.S. Cl. .................................... 549/534; 549/536; 502/348; 568/473
[58] Field of Search ................ 549/534, 536; 502/347, 502/348

[56] References Cited

U.S. PATENT DOCUMENTS

| 925,193 | 12/1886 | Wigman . | |
|---|---|---|---|
| 925,195 | 12/1886 | Meima . | |
| 2,424,085 | 7/1947 | Bergsteinsson et al. | 502/347 X |
| 3,663,455 | 5/1972 | Calcagno et al. | 549/536 X |
| 3,943,069 | 3/1976 | Antonelli et al. | 549/534 X |
| 3,957,690 | 5/1976 | Bobolev et al. | 549/533 X |
| 4,499,203 | 2/1985 | Toulhoat et al. | 502/247 |

FOREIGN PATENT DOCUMENTS

| 207541 | 1/1987 | European Pat. Off. . |
| 207542 | 1/1987 | European Pat. Off. . |
| 207550 | 1/1987 | European Pat. Off. . |
| 1137624 | 1/1957 | France . |

*Primary Examiner*—Patrick P. Garvin

[57] ABSTRACT

A supported silver catalyst having improved thermostability is prepared by depositing silver particles on a carrier or support having a stepped structure.

8 Claims, No Drawings

SILVER CATALYST AND A PROCESS FOR PREPARING SAME

This invention relates to a silver catalyst in which the silver is present on a thermostable inert carrier and a process for preparing same.

Silver catalysts are used in particular in selective oxidations of organic chemical compounds. Processes in which chemical compounds are prepared on a large scale by means of silver catalysts are the oxidation of ethylene to ethylene oxide and the oxidation of methanol to formaldehyde. In addition, silver catalysts are used in the (liquid-phase) oxidation of (unsaturated) aldehydes to the corresponding carboxylic acids, such as, for example, the oxidation of acrolein or methacrolein to acrylic acid and methacrylic acid, respectively.

A major drawback of the present silver catalysts is their relatively low activity and stability. The low stability gives the most difficulties from a technical point of view. As a result, the activity of the catalyst continuously decreases in use. By increasing the temperature of the reactor, the conversion can be kept at its level, albeit at the expense of a loss in selectivity. At a given moment, however, activity has declined to the extent that the consequential increase in temperature leads to an unacceptable decrease in selectivity. The reactor must then be taken offstream so that the catalyst may be replaced by a fresh catalyst. As the replacement of the catalyst is time-consuming this leads to a considerable loss in production. Consequently, it is highly desirable to have a catalyst which, owing to better stability, permits longer service periods.

The relatively low activity of silver catalysts according to the state of the prior art is also a drawback. The low activity is caused by the catalysts containing relatively large silver particles. As a consequence, a relatively large amount of silver is needed in order to realize the silver area in the reactor necessary for the technically required conversion. The result is that the investment involved in the silver catalyst is high. The availability of catalysts with a higher thermostable silver area per unit weight of silver would render it possible to considerably decrease investments.

Therefore, it would be highly desirable to provide a silver catalyst with a higher thermostability and a larger silver area per unit weight of silver.

SUMMARY OF THE INVENTION

The present invention is such a silver catalyst comprising (1) a thermostable, inert carrier (support) wherein at least about one percent of the carrier surface has a stepped structure and (2) finely divided silver particles deposited on the surface of the carrier.

It has been found that silver catalysts in which the silver is applied to a carrier of which at least about 1 percent and preferably at least about 5 percent of the carrier area is provided with steps or has a stepped structure, exhibit a surprisingly higher thermostability than the conventional silver catalysts. By "steps" or "stepped structure", it is meant that such portion of the carrier surface has a fair-step structure or a terrace structure with sharp (square) rather than rounded edges. As small silver particles are stabilized by the steps on the carrier, the silver area and hence the activity per unit weight of silver is also larger than in silver catalysts of the prior art. It has further been found that the surprising improvement of the silver catalysts obtained according to the invention already occurs when the steps on the carrier material are just a few atomic layers high. In fact, even then, the mobility (movement) of silver particles on the carrier surface is effectively prevented.

Although there is no certainty about this reduced mobility of silver particles, the available data suggest that the movement of the silver particles deposited on a carrier as such leads to a decrease of the silver area. The movement of the silver particles over the carrier surface is analogous to the Brown movement which colloidal particles perform in a liquid. When thus moving silver particles come into contact with each other, they rapidly coalesce to form a larger silver particle with a smaller area than that of the original silver particles. The rapid coalescence of metal particles, which are solid and not liquid, is caused by the large mobility of metal atoms over metal surfaces. The driving force for the coalescence is the reduction in area and the area energy inherent therein.

The silver catalysts produced in accordance with the invention are distinguished by a high thermal stability. This renders these catalysts highly suitable for the selective oxidation of ethylene to ethylene oxide. Moreover, the catalysts according to the invention exhibit a high selectivity for the formation of ethylene oxide, especially after a thermal pretreatment at high temperature.

DETAILED DESCRIPTION OF ILLUSTRATIVE EMBODIMENTS

The carrier or support suitably employed in the silver catalyst is made by heating the carrier to a temperature of, for example, about 1000° C. or higher. If α-aluminum oxide is used as the carrier, steps can be formed thereon by keeping it at a temperature of, e.g., about 1100° C. or higher for several hours prior to loading with silver. A larger fraction of steps in the surface, however, is obtained by pre-treating the α-aluminum oxide carrier with an acid. It has been found that by treating α-aluminum oxide with acid, originally rounded corners and edges of the aluminum oxide particles acquire a structure in which terraces and steps occur. A study in the scanning electron microscope has shown this. The treatment with an acid can be effected with various acids, such as hydrochloric acid, nitric acid, phosphoric acid, sulfuric acid and organic acids, such as oxalic acid, with a pK value of no more than 3. The concentration of the acid is preferably taken between 0.4N and 0.001N. In connection with the use as a catalyst and with the subsequent application of silver to the pre-treated carrier, the acid-treated carrier will have to be thoroughly washed in most cases to remove all residues of the acid used as completely as possible. The treatment with acid is advantageously carried out by suspending the carrier in an aqueous solution of the acid. The process is not limited to aqueous solutions, but other solvents may be used. Aqueous solutions, however, are preferred. Carriers or supports made from other compositions such as silica, titania, zeolites and the like, can also be suitably employed.

Loading a carrier having the desired stepped structure in its surface can be effected in various ways well known to those skilled in the art. One suitable possibility is for the carrier to be impregnated with a solution of a silver compound, followed by removing the solvent by evaporation. Examples of suitable silver compounds include silver nitrate, silver perchlorate, silver-ammonia complexes and other silver salts and complexes that are soluble in aqueous or other suitable liquid media. It is also possible to start from a suspension of carrier in a solution of silver compound, and reduce the dissolved silver with a compound such as formaldehyde or glucose to form metallic silver. The metallic silver is then deposited on the carrier. The invention is illustrated in and by the following examples.

EXAMPLE 1

This example demonstrates the decrease in mobility of silver particles on a stepped surface of an aluminum oxide carrier.

First silver particles are applied to an α-aluminum oxide carrier whose surface contains very few steps, if any at all. Subsequently, another portion of the same carrier material is treated with hydrochloric acid; the pH of the hydrochloric acid is 0.5 and the carrier is suspended in this acid for 17 hours. As will be explained hereinafter, this treatment so attacks the carrier surface at the rounded corners and edges as to form steps there. Finally, silver particles are applied to the pre-treated and carefully washed carrier in a manner identical to the non-pre-treated carrier. The silver particles are obtained by the reduction of silver ions with formaldehyde in the presence of the suspended carrier.

When the two catalysts are viewed in the scanning electron microscope a homogeneous distribution of the silver throughout the entire carrier material is shown. After calcination of both catalysts in air at a temperature of 850° C. for 19 hours, it is observed that, whereas both laden carriers exhibit the same uniform distribution of silver particles over the carrier surface before the thermal treatment, the distributions for the two catalysts are quite different after the thermal treatment. In the carrier pre-treated with acid, the silver particles, after the thermal treatment, are present on those parts of the surface of the carrier where steps are present. In the carrier not pre-treated with acid, where steps hardly, if at all, occur in the surface, the thermal treatment leads to excessive sintering of the silver. It has been found that a fraction of 1 percent of the carrier surface covered with steps is sufficient to provide an appreciable improvement in thermal stability. Preferably, this fraction is 5 percent or more.

EXAMPLE 2

As carrier material is used α-aluminum oxide (purum) of Fluka A.G. (CH-9470 Buchs). This material has a specific area of 0.8 $m^2/g$ and only possesses macropores. A 28.0-g portion of this material is suspended in an aqueous solution of hydrochloric acid with a pH of about 0.5, and kept in the solution for about 20 hours. The carrier is then filtered and thoroughly washed with deionized water until no chlorine ions can be demonstrated in the eluent. The carrier is subsequently dried at 120° C. for about 2 hours.

The carrier thus pre-treated is suspended in an oxygen-free ammoniacal silver solution with a pH of about 10.5. This solution is prepared by dissolving 3.8 g silver nitrate in 1500 ml water and then, with stirring, adding a little concentrated ammonia (25 percent by weight). The amount of ammonia is just sufficient to form the ammoniacal silver complex. After stabilization of the suspension for 1 hour, 20 ml concentrated formaldehyde (35 percent by weight) is slowly injected into the suspension with vigorous stirring. The reduction of the silver ions proceeds virtually instantaneously. After completion, the catalyst is filtered off and dried at 120° C. for about 20 hours. The catalyst thus prepared contains 7.9 percent by weight of silver.

The activity of the dried silver-laden α-aluminum oxide powder for the oxidation of ethylene is investigated. For this purpose, 4.3 g of the powder is pressed to form pellets having sizes of 1-2 mm. The catalyst is introduced into a tubular reactor 20 cm long and 8.4 mm in diameter.

A mixture of 5 percent by volume of carbon dioxide, 18 percent by volume of ethylene, 8 percent by volume of oxygen and the balance of nitrogen is passed over the catalyst at a pressure of 4 ats. at the rate of 100 ml (stp) of this gas mixture over the catalyst per minute. Ethylene dichloride (1 ppm) is previously added to the gas mixture as a moderator. No alkali metal, or alkaline earth metal promoter is added to the catalyst.

At a temperature of 250° C., the selectivity for the conversion of ethylene into ethylene oxide is about 80 percent at an ethylene conversion of about 5 percent.

To determine the thermal stability of the catalyst, another quantity of the powdered silver-laden carrier is kept at 850° C. for 19 hours. This temperature is considerably higher than that at which silver catalysts are normally used. Therefore, an excellent impression of the thermal stability of the silver catalyst according to the invention can be obtained in a relatively short period of time, in this case 19 hours.

A 4.0-g portion of the powder thus thermally treated is pressed to form pellets (sizes 1 mm-2 mm) and introduced into the above described reactor. A mixture of 5 percent by volume of carbon dioxide, 18 percent by volume of ethylene, 8 percent by volume of oxygen and the balance of nitrogen is passed over the catalyst at a pressure of 4 ats. Ethylene dichloride (1 ppm) is previously added to the gas mixture at a moderator. Again, no alkali metal or alkaline earth metal promotor is added.

Under these reaction conditions, at a reactor temperature of 280° C., a selectivity for the conversion of ethylene into ethylene oxide of more than 75 percent is measured at a conversion of about 8 percent.

COMPARATIVE EXAMPLE 3

In the same way as described in Example 2, a catalyst is prepared, but the carrier is not previously treated with an acid.

The catalyst is prepared, starting from 27.8 g carrier material and 3.82 g silver nitrate. Ultimately, the catalyst contains 8.0 percent by weight of silver. The reactor is loaded in the same manner as described above, and the reaction mixture is also identical to that described above, and the reaction mixture is also identical to that described above. At a temperature of 220° C., the selectivity for the conversion of ethylene into ethylene oxide of the (fresh) catalyst not thermally treated is about 80 percent at an ethylene conversion of about 4 percent. After a thermal treatment at 850° C. in air for 19 hours, at a reactor temperature of 280° C., a selectivity of about 65 percent is measured with an ethylene conversion of about 4 percent.

The above examples show that, by providing steps on the α-aluminum surface, the thermal stability of the silver particles has been increased. Although the differences between the two 'fresh' catalysts are not large, the superiority of the catalyst according to the invention is apparent after the thermal pre-treatment at 850° C. Both a higher activity and a higher selectivity is observed with the catalyst prepared according to the invention.

What is claimed:

1. A process for the catalytic selective oxidation of ethylene to ethylene oxide which process comprises contacting ethylene with oxygen in the presence of a catalytic amount of a catalyst under conditions sufficient to convert the ethylene to ethylene oxide, said catalyst comprising a thermostable, inert carrier consisting essentially of alpha-aluminum oxide to which finely-divided silver partices have been applied, said carrier having a surface wherein at least about 1 percent of the carrier surface is provided with a stepped structure as a result of treatment of the carrier with acid.

2. The process of claim 1 wherein at least about 5 percent of the carrier surface is provided with a stepped structure.

3. The process of claim 2 wherein the carrier is heated at a temperature higher than 1000° C. prior to loading with silver particles.

4. The process of claim 2 wherein the carrier is washed with water after the treatment with acid.

5. The process of claim 4 wherein the carrier is washed until no acid residues from the treatment with acid can be demonstrated in the washing water.

6. The process of claim 5 wherein an acid having a $pK_a$ of less than or equal to 3 is used.

7. The process of claim 6 wherein the acid is selected from the group consisting of HCl, $HNO_3$, $H_3PO_4$, $H_2SO_4$ and oxalic acid.

8. The process of claim 7 wherein the carrier is treated with a solution of an acid having a pH of less than 4.

* * * * *